United States Patent
Wu et al.

(10) Patent No.: US 9,134,358 B2
(45) Date of Patent: Sep. 15, 2015

(54) CABLE FATIGUE MONITOR AND METHOD THEREOF

(75) Inventors: Gang Wu, Shanghai (CN); Jens Hofschulte, Lehrte (DE); JingGuo Ge, Shanghai (CN)

(73) Assignee: ABB RESEARCH LTD., Zurich (CH)

( * ) Notice: Subject to any disclaimer, the term of this patent is extended or adjusted under 35 U.S.C. 154(b) by 281 days.

(21) Appl. No.: 13/820,380

(22) PCT Filed: Nov. 9, 2010

(86) PCT No.: PCT/CN2010/078566
§ 371 (c)(1),
(2), (4) Date: Mar. 1, 2013

(87) PCT Pub. No.: WO2012/061979
PCT Pub. Date: May 18, 2012

(65) Prior Publication Data
US 2013/0154676 A1    Jun. 20, 2013

(51) Int. Cl.
*G01R 31/02*     (2006.01)
*B60L 5/00*      (2006.01)
*H02G 11/00*     (2006.01)
*G05B 23/02*     (2006.01)

(52) U.S. Cl.
CPC .......... *G01R 31/021* (2013.01); *B60L 5/00* (2013.01); *G05B 23/0256* (2013.01); *H02G 11/00* (2013.01)

(58) Field of Classification Search
USPC .......................... 324/544, 551, 543, 537, 522
See application file for complete search history.

(56) References Cited

U.S. PATENT DOCUMENTS

| | | |
|---|---|---|
| 5,185,684 A | 2/1993 | Beihoff et al. |
| 5,637,241 A | 6/1997 | Moates |
| 5,911,893 A * | 6/1999 | Kilty et al. ............... 219/130.21 |
| 2011/0260735 A1* | 10/2011 | McCabe et al. ............... 324/543 |

FOREIGN PATENT DOCUMENTS

| | | |
|---|---|---|
| CN | 201255757 Y | 6/2009 |
| EP | 0639879 A2 | 2/1995 |
| JP | 9168226 A | 6/1997 |

OTHER PUBLICATIONS

The State Intellectual Property Office, P.R. China, International Search Report re International Application No. PCT/CN2010/078566, dated Jul. 21, 2011.

* cited by examiner

*Primary Examiner* — Tung X Nguyen
*Assistant Examiner* — Alesa Allgood
(74) *Attorney, Agent, or Firm* — Robert A. Jefferis; Driggs, Hogg, Daugherty & Del Zoppo Co., LPA

(57) ABSTRACT

A monitor for determining the operation condition of at least one cable that suffers bending and/or twisting and constitutes an electrical loop and a method thereof are provided. The monitor comprises a test electrical signal generator (5) for generating an identifiable test electrical signal and injecting the test electrical signal into the first point of the at least one cable, a test electrical signal filter (7) adapting to extract the injected test electrical signal from the second point of the at least one cable, and a comparator (8) for comparing a predetermined threshold with the difference between the electrical state of the injected test electrical signal and the extracted test electrical signal and producing a warning signal indicating cable fatigue when the difference exceeds the predetermined threshold. It provides the advantages as follows: it only monitors the electric performance, not the mechanical performance of a cable; it monitors the cable itself rather than a monitor material; it is applicable to all kinds of cables, including but not limited to a large-current cable; it does not introduce new cables; it is an on-line monitoring, i.e. the electromechanical system needs no pause for monitoring its cable fatigue.

14 Claims, 6 Drawing Sheets

CABLE FATIGUE MONITOR AND METHOD THEREOF

RELATED APPLICATION

This application is a national filing of PCT application Serial No. PCT/CN2010/078566, filed Nov. 9, 2010.

TECHNICAL FIELD

The invention relates to cable monitor and the method thereof, and more particularly to cable monitor for cable fatigue caused by bending and/or twisting and the method thereof.

BACKGROUND ART

Cable is widely used for industrial equipment/devices to transfer working load. Working load can be power, analogue data or digital data. When a cable gets fatigued, it can no longer transfer well and will possibly make the equipment/device breakdown.

Cable fatigue is caused by cable-bending and/or cable-twisting occurred in a motion system, such as in an industrial robot. An industrial robot (manipulator) has several joints. When it works, its joints rotate quickly, thus the cables in it or attached to it bend or twist quickly. Therefore, an industrial robot is easier to have its cables fatigued, thus the risk of breakdown is high.

A conventional solution to cable fatigue is prediction, i.e. to predict the fatigue-life of a cable and replace it just before it cannot work. The prediction cannot be accurate enough because of the reasons:

According to the S-N curve (S means stress, N means the number of bending/twisting before a component breaks. S-N curve is a curve illustrating the relation between the stress applied on a component and the fatigue-life of the component), a little change of stress can cause a big change of fatigue-life. For example, 3% change of stress causes 30% change of fatigue-life. However, it costs too much to simulate the stress accurately enough, thus a large error of fatigue-life is unavoidable for practical operation.

The anti-fatigue performance (the relation between stress and fatigue-life) of any two cables is different, even if the two cables are of the same batch, by the same factory. The difference will be larger if the two cables are made by different factories. It is impractical for a robot producer to test the cables' anti-fatigue performance frequently. Therefore, a robot producer does not know exactly the anti-fatigue performance of the cables because the cables are of different batches or made by different cable suppliers. The result is that even if we simulate the stress very accurately, we still cannot predict the fatigue-life accurately.

The other conventional solution is to monitor cable fatigue and replace the cable when it cannot work well. It is more practical than prediction and there have been some attempts. The patent Arc Welding Method and Apparatus with Power Cable Fatigue Monitor (Patent No. US005911893A) gives a method to monitor cable fatigue, i.e. monitoring the voltage drop over the power cable. The power cable should retire when the voltage drop exceeds a threshold. The drawbacks of this patent include:

Considering the small resistance of a power cable, a very large current is necessary to make the voltage drop measurable. However, it is impossible to transfer so large current over a normal cable. Therefore, this patent is only applicable for arc welding power cable. It is not suitable to most applications such as data cable or motor power cable.

This patent introduces new cables (component 66 and 67 in FIG. 7 of this patent) to measure the voltage drop, which increase the risk of fatigue.

The patent Welder Cable Monitor (Patent No. US005637241A) is similar to the previous patent.

There are several existing patents to monitor with mechanical performance. Of course the component can be a cable. Here are some of them:

Remote and Powerless Miniature Fatigue Monitor and Method (Publication No. U.S. Pat. No. 5,531,123A);

Fatigue Monitor for Small-diameter Piping Joint (Publication No. JP61110029A);

Monitor Material, Method for Measuring Fatigue Damage Degree Using the Same, and Machine Part with Monitor Material (Publication No. JP2001201432A);

Fatigue Damage Monitor Gauge and Fatigue Damage Monitor Device (Publication No. JP10111267A);

Monitor for Detecting Fatigue Damage Monitor (Publication No. JP5113390A)

Fatigue Monitor of Rotating Shaft (Publication No. JP54116986A); and

Strain Gauge Having Double Function as Fatigue Aging-monitor (Publication No. JP7218214A).

These patents still have some drawbacks because:

What they monitor is the mechanical performance but not the electrical performance. Usually during the process of fatigue, a cable loses its electrical performance sooner than losing its mechanical performance, i.e. it is not suitable to transfer power/data but the degradation of its mechanical performance is very little. Hence, a cable may be eligible according to these patents but in fact it should retire.

Some of these patents attach a piece of monitor material to the monitored component. The monitor material is a reference to estimate the fatigue damage on the monitored component. However, a robot doesn't have too much room for the monitor material. It is not suitable to detach the monitor material for testing because the robot is always busy. Besides, the difference between the monitor material and the monitored component introduces a new error. What's more, if an industrial robot manufacture wants to apply these patents, it must turn to a cable supplier for cable with monitor material. Hence, the robot producing company might lose its vantage point in business.

According to the other conventional technologies, engineers test the fatigue-life of a cable by comparing the initial resistance of a cable with the value after bending/twisting. A large enough degeneration means that the cable is fatigued. For example, the initial resistance of a cable was 0.493 ohm. The resistance became 0.702 ohm after bending/twisting the cable for 3,818,090 times. Hence, the engineers know that the fatigue-life of this batch of cable is about 3.8 million cycles. However, there is no working load over the sample cable and the engineers can measure the resistance with a multimeter. For a cable installed in a robot, the working load over it will disturb the multimeter so the resistance is not measurable.

BRIEF SUMMARY OF THE INVENTION

It is therefore an objective of the invention to provide a monitor for determining an operation condition of at least one cable that suffers bending and/or twisting and constitutes an electrical loop, comprising: a test electrical signal generator, for generating a test electrical signal identifiable and injecting the test electrical signal into a first point of the at least one cable; a test electrical signal filter, be adapted to extract the injected test electrical signal from a second point of the at least one cable; and a comparator, for comparing a predetermined threshold with the difference between the electrical state of the injected test electrical signal and the extracted test electrical signal, and producing a warning signal indicating cable fatigue when the difference exceeds the predetermined threshold.

It is therefore another objective of the invention to provide a method for determining an operation condition of at least one cable that suffers bending and/or twisting and constitutes an electrical loop, comprising:
  (a) generating a test electrical signal identifiable and injecting the test electrical signal into a first point of the at least one cable;
  (b) extracting the injected test electrical signal from a second point of the at least one cable; and
  (c) comparing a predetermined threshold with the difference between the electrical state of the injected test electrical signal and the extracted test electrical signal, and producing a warning signal indicating cable fatigue when the difference exceeds the predetermined threshold.

By having a monitor with such configuration and/or a method thereof, present invention at least provides the advantages as follows:
  (a) it only monitors the electric performance, not the mechanical performance of a cable;
  (b) it monitors the cable itself rather than a monitor material;
  (c) it is applicable to all kinds of cables, including but not limited to large-current cable;
  (d) it does not introduce new cables;
  (e) it is an on-line monitoring, i.e. the electro-mechanical system needs no pause for monitoring its cable-fatigue.

BRIEF DESCRIPTION OF THE DRAWINGS

The subject matter of the invention will be explained in more detail in the following text with reference to preferred exemplary embodiments which are illustrated in the drawings, in which.

The reference symbols used in the drawings, and their meanings, are listed in summary form in the list of reference symbols. In principle, identical parts are provided with the same reference symbols in the figures.

PREFERRED EMBODIMENTS OF THE INVENTION

Figure 1A:
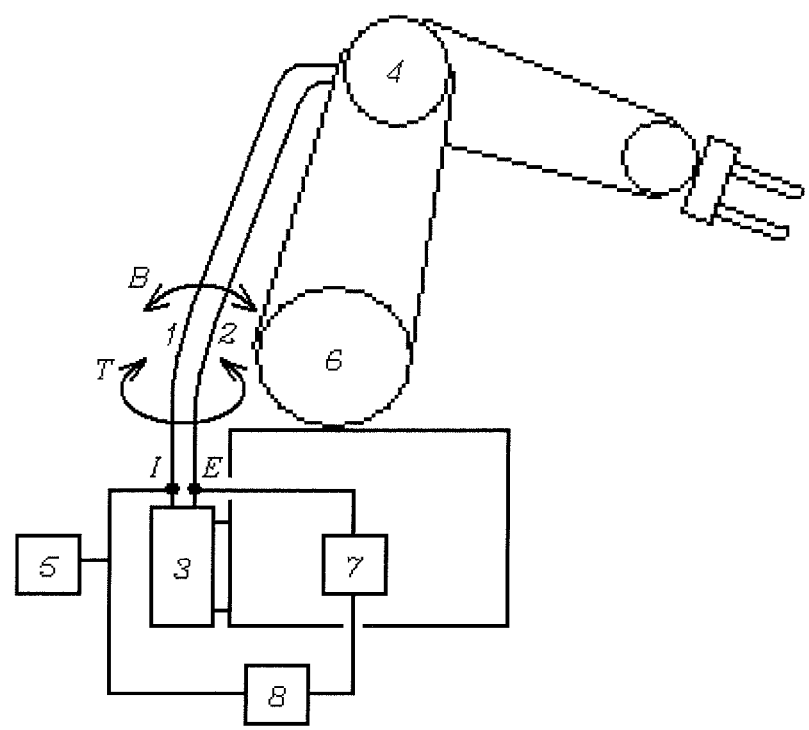
FIG. 1A illustrates an electro-mechanical system according to an embodiment of present invention.

FIG. 1A illustrates an electro-mechanical system according to an embodiment of present invention. Particularly, such electro-mechanical system may be an industrial robot, which includes an electrical loop formed in series with a first cable 1, a first electrical part 3, a second cable 2, and a second electrical part 4.

For example, the first electrical part 3 may be a controller or a power supply, and the second electrical part 4 may be a sensor or a motor, and the first electrical part 3 and the second electrical part 4 are disposed at different side of a joint 6. By having such arrangement with the joint 6, there is a relative rotation between the first electrical and the second electrical part 3, 4, and therefore with the relative rotation a bending and/or twisting occurs of the first and second cables 1,2 electrically linking the first and the second electrical parts 3, 4. Such bending and/or twisting are indicated by arrow B and arrow T in FIG. 1A.

Figure 1B:
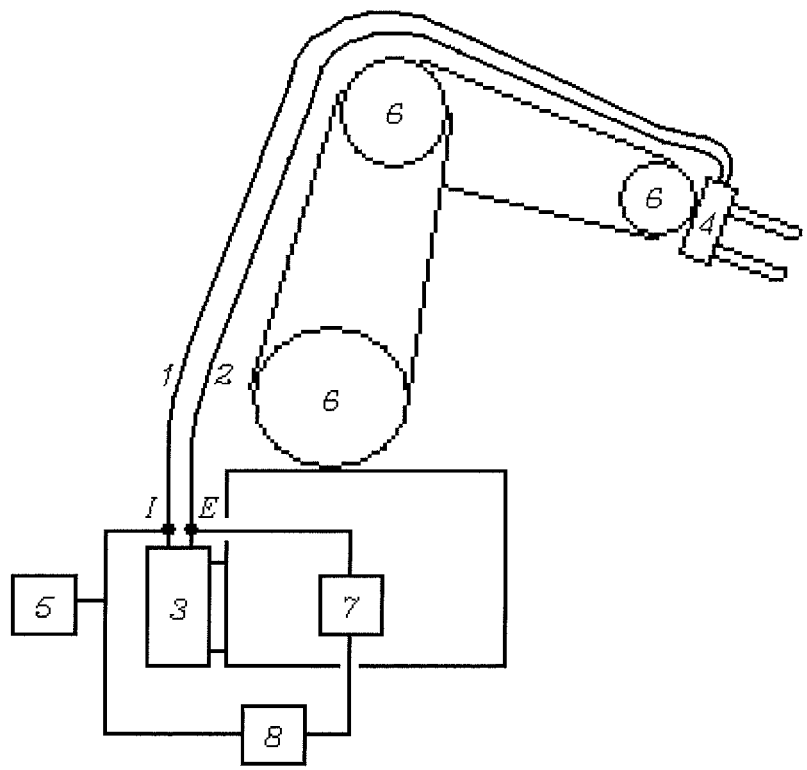
FIG. 1B illustrates an electro-mechanical system according to another embodiment of present invention.

FIG. 1B illustrates an electro-mechanical system according to another embodiment of present invention. Alternatively, there may be more than one joints 6 disposed between the first and the second electrical parts 3, 4 with more than two rotational degrees of freedom. By having such arrangement with more than one joint, there is a bending and/or twisting suffered by the first and the second cables 1, 2 electrically linking them.

Figure 1C:
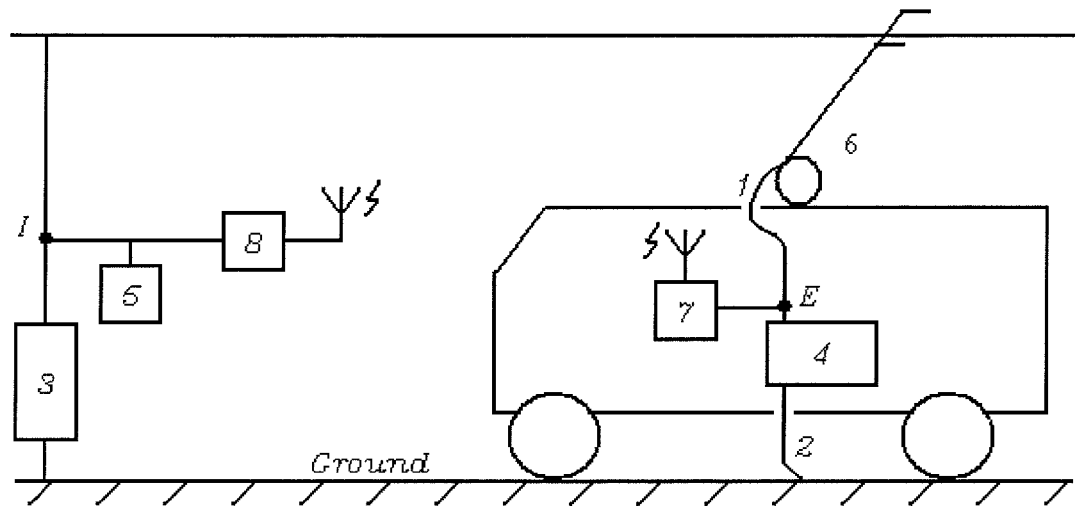
FIG. 1C illustrates an electro-mechanical system according to another embodiment of present invention.

FIG. 1C illustrates an electro-mechanical system according to another embodiment of present invention. Particularly, such electro-mechanical system may be an electrical vehicle, which includes an electrical loop formed in series with a first cable 1, a first electrical part 3, a second cable 2, and a second electrical part 4.

For example, the first electrical part 3 may be a controller or a power supply, and the second electrical part 4 may be a sensor or a motor, and the first electrical part 3 and the second electrical part 4 are disposed at different side of a joint 6. By having such arrangement with the joint 6, there is a bending and/or twisting occurs of the first cable 1 electrically linking the first and the second electrical parts 3, 4. The working load loop is formed of a first cable 1, a first electrical part 3, the ground, a second cable 2 and a second electrical part 4. A monitor for determining an operation condition of the first cable 1 suffering the bending and/or twisting comprises a test electrical signal generator 5, a test electrical signal filter 7, and a comparator 8. And, the test electrical signal filter 7 and the comparator 8 are coupled by radio.

As shown in FIGS. 1A and 1B, the test electrical signal generator 5 is electrically connected with a first point I of the first cable 1, generates a test electrical signal identifiable and injects the test electrical signal into the first point I, and outputs the test electrical signal to the comparator 8. The test electrical signal may be identified by its unique electrical parameter, such as frequency. The test electrical signal filter 7 is electrically connected with a second point E of the second cable 2, extracts the injected test electrical signal from a second point E of the second cable 2, and outputs the exacted to the comparator 8. The comparator 8 compares a predetermined threshold with the difference between the electrical state (such as the voltage or current, or the attenuation and/or flutter thereof) of the injected test electrical signal and the extracted test electrical signal, and produces a warning signal indicating cable fatigue when the difference exceeds the predetermined threshold.

By having such a configuration of a monitor for determining cable-fatigue, present invention at least provides the advantages as follows:

it only monitors the electric performance, not the mechanical performance of a cable;

it monitors the cable itself rather than a monitor material;

it is applicable to all kinds of cables, including but not limited to large-current cable;

it does not introduce new cables;

it is an on-line monitoring, i.e. the electro-mechanical system needs no pause for monitoring its cable-fatigue.

As shown in FIGS. 1A and 1B, the test electrical signal generator 5, the test electrical signal filter 7 and the comparator 8 are arranged on the same side with respect to joint 6 (the location where the cables are bent and/or twisted), for example at the first electrical part side.

By having such arrangement of the components, the leads linking the test electrical signal generator 5, the test electrical signal filter 7 and the comparator 8 will not bend and/or twist with the bending and/or twisting of the first cable 1 and the second cable 2. Therefore, the leads have a relative long life due to non-bending and/or non-twisting.

As shown in FIG. 1C, the test electrical signal generator 5 is electrically connected with a first point I of the first cable 1, generates a test electrical signal identifiable and injects the test electrical signal into the first point I, and outputs the test electrical signal to the comparator 8. The test electrical signal may be identified by its unique electrical parameter, such as frequency. The test electrical signal filter 7 is electrically connected with a second point E of the first cable 1 extracts the injected test electrical signal from a second point E of the second cable 2, and outputs the exacted to the comparator 8. The comparator 8 compares a predetermined threshold with the difference between the electrical state (such as the voltage or current, or the attenuation and/or flutter thereof) of the injected test electrical signal and the extracted test electrical signal, and produces a warning signal indicating cable fatigue when the difference exceeds the predetermined threshold.

Such configuration according to FIG. 1C will bring about similar advantages as above.

In a preferred embodiment, for the avoidance of bending and/or twisting of the leads linking the components of the monitor, the first point I and the second point E are selected also at the same side with respect to the joint.

Figure 2A:
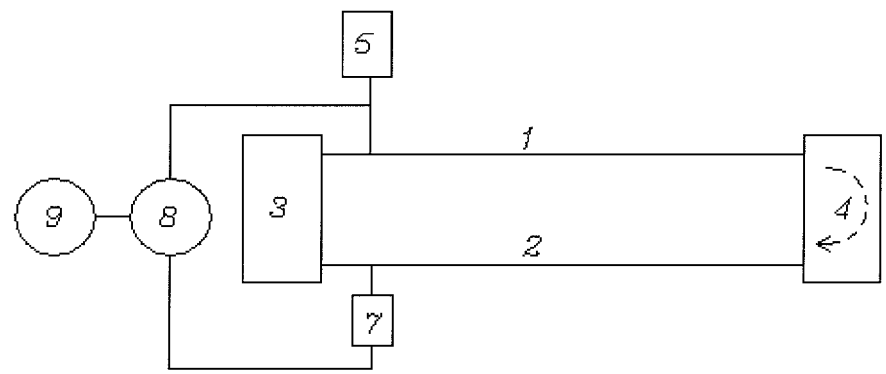
FIG. 2A illustrates an electrical structure of a monitor according to an embodiment of present invention.

FIG. 2A illustrates an electrical structure of a monitor according to an embodiment of present invention. Same reference number in the figures indicates the same component. As shown in FIG. 2A, the first cable 1 and the second cable 2 are between the first electrical part 3 and the second electrical part 4. When the robot works, cable 1 and cable 2 bend and twist. The first electrical part 3 and the second electrical part 4 apply working load to the first cable 1 and the second cable 2. The dot line arrow is the direction of the working load. A data storage component 9 electrically connects to the comparator 8.

Alternatively, the second cable 2 may be replaced with ground corresponding to the description as above.

Figure 2B:
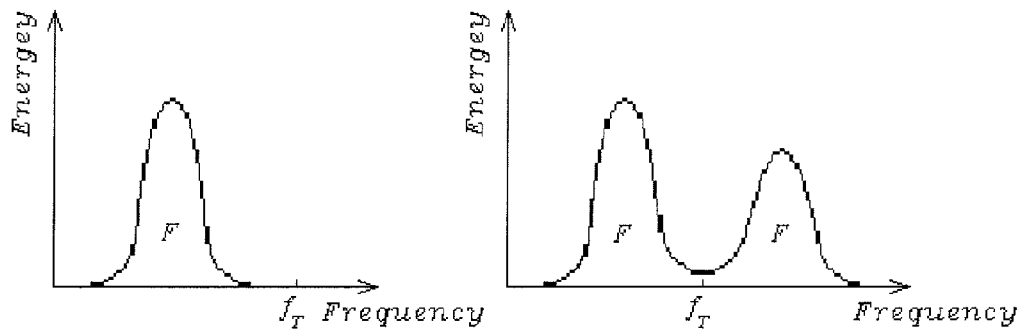
FIG. 2B illustrates the selection of the frequency of the test electrical signal in consideration of the spectrum of the working load according to an embodiment of present invention.

FIG. 2B illustrates the selection of the frequency of the test electrical signal in consideration of the spectrum of the working load according to an embodiment of present invention.

As shown in FIG. 2B, the spectrum of the working load carried by the electrical loop covers a spectrum F, which is measurable. For the purpose of keeping the test electrical signal identifiable, namely, to prevent the test electrical signal from interacting with the working load, the test electrical signal is set at frequency $f_T$ and the component of the working load at frequency $f_T$ is sufficiently small as compared to the component of the test electrical signal at frequency $f_T$. The test electrical signal filter, whose centre frequency is also $f_T$, is able to exact the test electrical signal at frequency $f_T$ without or with least noise. For example, the test electrical frequency $f_T$ is arranged to fall out of the spectrum F or at some interval in the spectrum F.

Figure 2C:
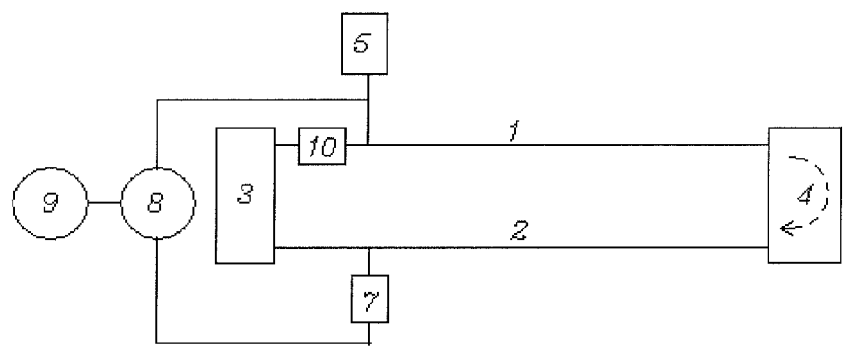
FIG. 2C illustrates an electrical structure of a monitor according to another embodiment of present invention.

FIG. 2C illustrates an electrical structure of a monitor according to another embodiment of present invention. The monitor further comprises a notch filter 10 with centre frequency at $f_T$. The notch filter 10 is arranged in the electrical loop, for preventing the test electrical signal from being disturbed by the working load. Even if there is an obvious component at $f_T$ in F, the component is eliminated by the notch filter so it cannot disturb said test electrical signal. Hence, the precision of comparator is improved.

Figure 3:
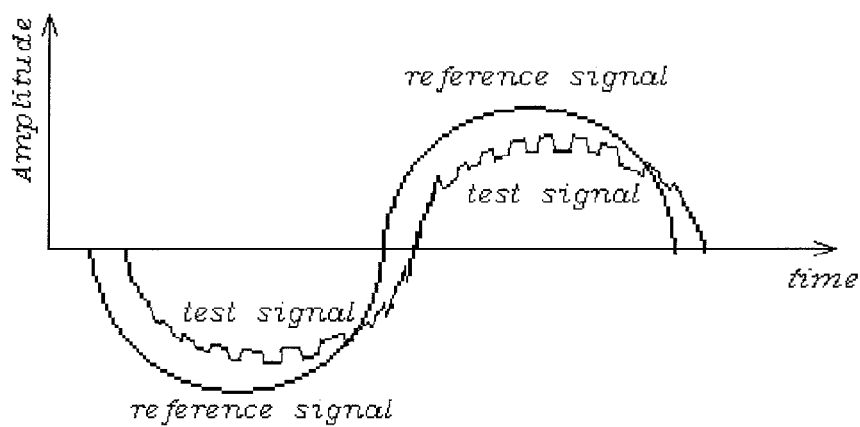
FIG. 3 illustrates the difference between the injected test electrical signal and the extracted test electrical signal.

FIG. 3 illustrates the difference between the injected test electrical signal and the extracted test electrical signal. The difference may be between amplitudes/flutter of voltage of the injected test electrical signal (reference signal) and the extracted test electrical signal (test signal). The process monitors the electric performance of a cable by measuring the attenuation and flutter of said test signal compared with said reference signal. There are many microcosmic damages in a cable when the cable get fatigued, which degrade the conductivity. Hence, the test signal attenuates more, i.e. the amplitude is smaller. On the other hand, when the cable is bending or twisting (because the robot is working), the displacement and deformation of these microcosmic damages also keep changing the conductivity. Hence, the test signal flutters, i.e. it is not smooth. Attenuation and flutter are the criterions to judge if the cables should retire. On the other hand, the phase of said test signal lags behind that of said reference signal because it runs over a longer path before entering the comparator 8.

In order not to interact with working load (power or data) over the monitored cable, the test signal works in a selected frequency (test frequency i.e. $f_T$), Test frequency is selected according to this rule: the energy of the working load at test frequency is weak enough. A filter extracts signal at test frequency for measurement. Because the energy of the working load at test frequency is weak enough, it is reasonable to treat the extracted signal as the test signal. It is also feasible to eliminate the energy of the working load with a notch filter whose center frequency equals the test frequency for higher precision. The amplitude of said test signal is not as large as that of said reference signal (attenuation). Said test signal is not as smooth as said reference signal (flutter). Either of or both of said attenuation and said flutter compose the difference between said test signal and said reference signal. On the other hand, the phase of said test signal lags behind that of said reference signal because it runs over a longer path before entering the comparator 8.

Figure 4A:
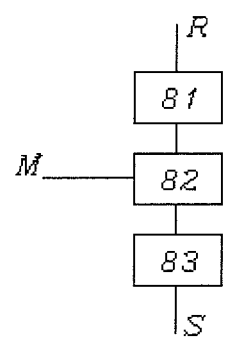
FIG. 4A illustrates a digital solution in frequency domain according to an embodiment of present invention.
Figure 4B:
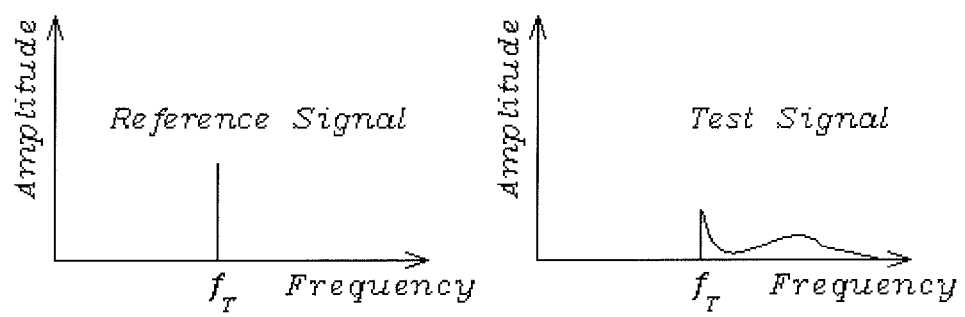
FIG. 4B illustrates the difference between two said spectrums according to an embodiment of present invention.
Figure 5:
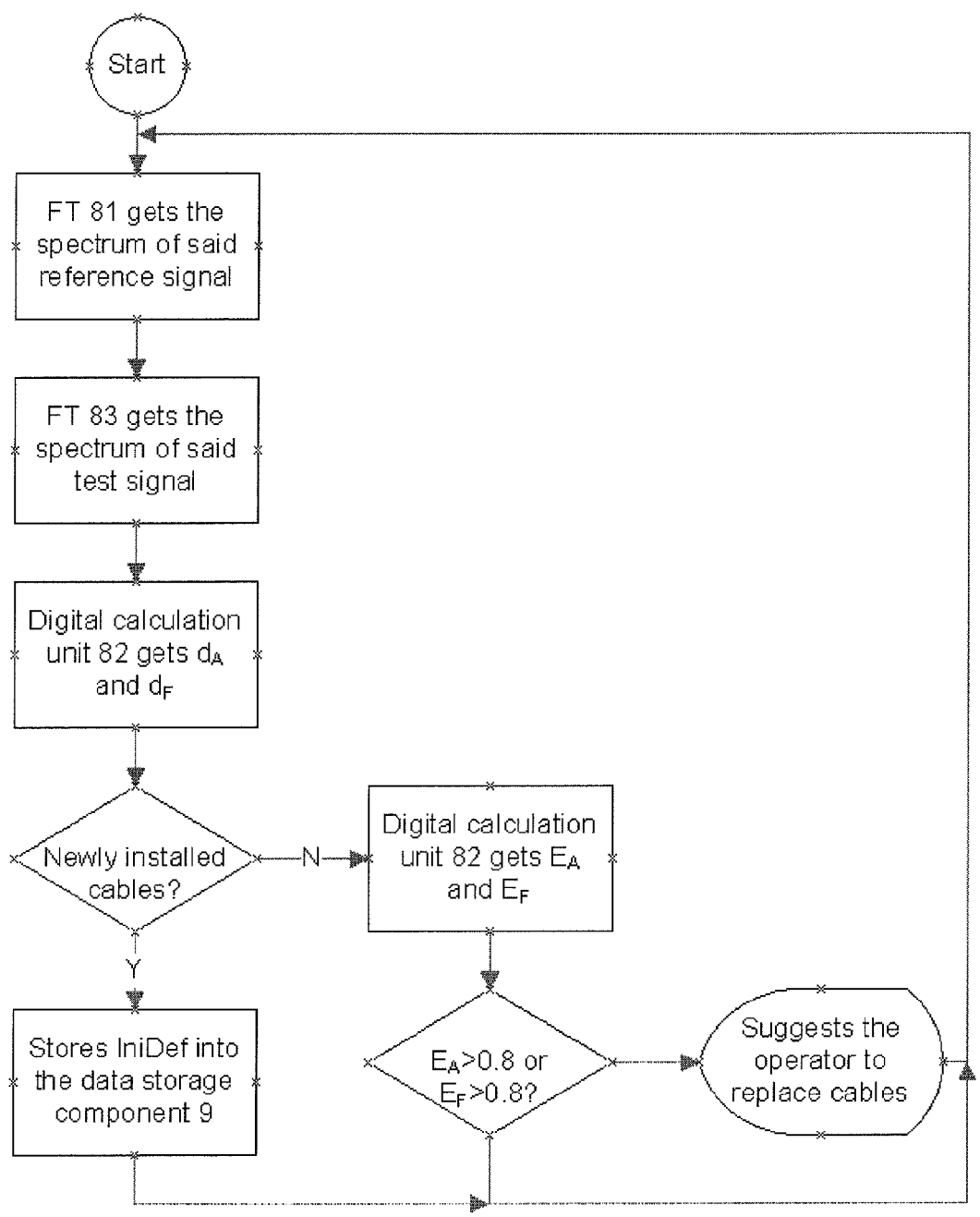
FIG. 5 shows a flow chart of a cable-fatigue monitoring process according to an embodiment of present invention.

The comparator 8 can be implemented with either digital or analog technique in either time domain or frequency domain. Any combination between digital/analog and time/frequency is feasible. FIG. 4A illustrates a digital solution in frequency domain as an example. The comparator 8 is composed of two Fourier Transformers (FT hereafter) 81, 83 and a digital calculation unit 82 in between. R is the entrance for said reference signal. S is the entrance for said test signal. M is the connection to the data storage component 9. FIG. 5 shows a flow chart of a cable-fatigue monitoring process according to an embodiment of present invention. The FT 81 gets the spectrum of said reference signal (FIG. 3) and feeds said spectrum to the digital calculation unit 82. The FT 83 gets the spectrum of said test signal (FIG. 3) and feeds said spectrum to the digital calculation unit 82. FIG. 4B illustrates the difference between two said spectrums. The calculation unit 82 measures the attenuation by calculating $d_A$ and measures the flutter by calculating $d_F$:

$d_A$=(the component of said test signal at $f_T$)   1.

/(the component of said reference signal at $f_T$)   2.

$d_F$=(the component of said test signal at $f_T$)/(the whole energy of said test signal)   3.

Hence, a vector ($d_A$, $d_F$) is enough for describing the difference between said test signal and said reference signal.

Just after the monitored cables are installed into the robot, comparator 8 stores said difference into the data storage component 9 with a title of "initial difference" (IniDif hereafter) because the monitored cable is brand new. Usually, both $d_A$ and $d_F$ in IniDif should be almost one. IniDef will not change until new cables replace the monitored cables.

When the robot is working, comparator 8 measures the current difference and compares it with IniDif stored in the data storage component 9. When said monitored cable's electrical performance degenerates gradually, $d_A$ and $d_F$ is smaller and smaller. A vector ($E_A$, $E_F$) is enough for describing the error between said current difference and IniDef:

$E_A$=(current $d_A$)/(the $d_A$ of IniDef)   1.

$E_F$=(current $d_F$)/(the $d_F$ of IniDef)   2.

When $E_A$ and/or $E_F$ is less than a threshold, say 0.8, comparator 8 gives a warning suggesting that the monitored cable should retire.

Figure 6:
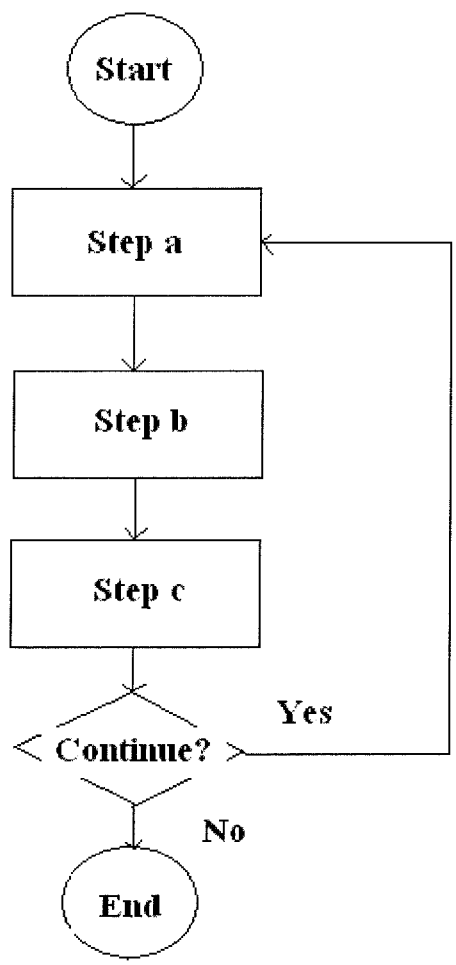
FIG. 6 shows a flow chart of a method for determining an operation condition of cable-fatigue according to an embodiment of present invention.

FIG. 6 shows a flow chart of a method for determining an operation condition of cable-fatigue according to an embodiment of present invention. The method is carried out based on the electro-mechanical system as illustrated above. Step a, generating a test electrical signal identifiable and injecting the test electrical signal into a first point of the at least one cable, step b, extracting the injected test electrical signal from a second point of the at least one cable; and step c, comparing a predetermined threshold with the difference between the electrical state of the injected test electrical signal (reference signal) and the extracted test electrical signal (test signal), and producing a warning signal indicating cable fatigue when the difference exceeds the predetermined threshold. If we need to continuously monitoring the cable-fatigue, then goes back to step a, otherwise, goes to end.

For the advantages set forth above, the test electrical signal is set at frequency $f_T$, the test electrical signal filter's centre frequency is set at $f_T$, the electrical loop carries an working load dispersed on a spectrum F, and the component of F at frequency $f_T$ is sufficiently small as compared to the component of the test electrical signal at frequency $f_T$. For example, the test electrical frequency $f_T$ is arranged to fall out of the spectrum F or in the interval in the spectrum F.

For preventing the test electrical signal from being disturbed by the working load, step d is inserted before step a: filtering the working load with a notch filter whose centre frequency is at $f_T$. Even if there is an obvious component at $f_T$ in said working load, the component is eliminated by the notch filter so it cannot disturb said test electrical signal. Hence, the precision of comparator is improved.

Though the present invention has been described on the basis of some preferred embodiments, those skilled in the art should appreciate that those embodiments should by no way limit the scope of the present invention. Without departing from the spirit and concept of the present invention, any variations and modifications to the embodiments should be within the apprehension of those with ordinary knowledge and skills in the art, and therefore fall in the scope of the present invention which is defined by the accompanied claims.

The invention claimed is:

1. A monitor that determines an operation condition of at least one cable that suffers at least one of bending or twisting and constitutes an electrical loop, comprising:
   a test electrical signal generator that generates a test electrical signal and injects the test electrical signal into a first point of the at least one cable;
   a test electrical signal filter that extracts the injected test electrical signal from a second point of the at least one cable; and
   a comparator that compares a predetermined threshold with a difference between an electrical state of the injected test electrical signal and the extracted test electrical signal, producing a warning signal indicating cable fatigue in response to the difference exceeding the predetermined threshold;
   wherein:
   the test electrical signal is set at a first frequency;
   a center frequency of the test electrical signal filter is set at the first frequency;
   the electrical loop carries a working load dispersed on a predetermined spectrum; and
   a component of the working load at the first frequency is less than a component of the test electrical signal at the first frequency.

2. The monitor according to claim 1, wherein:
   the test electrical frequency falls out of the predetermined spectrum.

3. The monitor according to claim 1, wherein:
   one of said at least one cable, a first part, ground and a second part constitute the electrical loop; and
   the first point and the second point are arranged on said one cable.

4. The monitor according to claim 1, wherein:
   a first cable of said at least one cable, a first part, a second cable of said at least one cable and a second part constitute the electrical loop; and
   the first point and the second point are respectively arranged on the first cable and the second cable and the first point and the second point are arranged at a same end of said at least one cable with respect to the at least one of the bending or twisting portions of the cables.

5. The monitor according to claim 1, further comprising:
   a notch filter, with a center frequency at the first frequency, arranged in the electrical loop for preventing the test electrical signal from being disturbed by the working load.

6. The monitor according to claim 1, wherein:
   the working load is of at least one of power, or digital data, or analog data.

7. The monitor according to claim 1, wherein:
   the difference is at least one of an attenuation or a flutter of the extracted test electrical signal compared with the injected test electrical signal.

8. A method for determining an operation condition of at least one cable that suffers at least one of bending or twisting and constitutes an electrical loop, comprising:
   (a) generating a test electrical signal identifiable and injecting the test electrical signal into a first point of the at least one cable;

(b) extracting the injected test electrical signal from a second point of least one cable; and (c) comparing a predetermined threshold with a difference between an electrical state of the injected test electrical signal and the extracted test electrical signal, and producing a warning signal indicating cable fatigue when the difference exceeds the predetermined threshold;

wherein:

the test electrical signal is set at first frequency;

a center frequency of the test electrical signal filter is set at the first frequency;

the electrical loop carries a working load dispersed on a predetermined spectrum; and a component of a working load at the first frequency is less than a component of the test electrical signal at the first frequency.

9. The method according to claim 8, wherein:
the test electrical frequency falls out of the predetermined spectrum.

10. The method according to claim 8, wherein:
one of said at least one cable, a first part, ground and a second part constitute the electrical loop; and
the first point and the second point are arranged on said one cable.

11. The method according to claim 8, wherein:
a first cable of said at least one cable, a first part, a second cable of said at least one cable and a second part constitute the electrical loop; and
the first point and the second point are respectively arranged on the first cable and the second cable and are arranged at the same side with respect to the at least one of the bending or the twisting portions of the cables.

12. The method according to claim 8, further comprising step (d) before (a):
(d) arranging a notch filter, with a center frequency at the first frequency, in the electrical loop for the working load to prevent the test electrical signal from being disturbed by the working load.

13. The method according to claim 9, wherein:
the working load is at least one of power, analog data, or digital data.

14. The method according to claim 8, wherein:
the difference is at least one of an attenuation or a flutter of the extracted test electrical signal compared with the injected test electrical signal.

* * * * *